US008791309B2

(12) United States Patent
Zhai et al.

(10) Patent No.: US 8,791,309 B2
(45) Date of Patent: Jul. 29, 2014

(54) SYNTHESIS OF 3,3,3-TRIFLUOROPROPYNE

(71) Applicant: Honeywell International Inc., Morristown, NJ (US)

(72) Inventors: Yian Zhai, Amherst, NY (US); Andrew J. Poss, Kenmore, NY (US); Rajiv R. Singh, Getzville, NY (US); David Nalewajek, West Seneca, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/099,560

(22) Filed: Dec. 6, 2013

(65) Prior Publication Data

US 2014/0179961 A1 Jun. 26, 2014

Related U.S. Application Data

(60) Provisional application No. 61/745,078, filed on Dec. 21, 2012.

(51) Int. Cl.
*C07C 17/00* (2006.01)
*C07C 17/23* (2006.01)

(52) U.S. Cl.
CPC .................................... *C07C 17/23* (2013.01)
USPC .......................................... 570/156; 570/155

(58) Field of Classification Search
USPC .................................................. 570/155, 156
See application file for complete search history.

(56) References Cited

U.S. PATENT DOCUMENTS

| | | | |
|---|---|---|---|
| 7,964,759 | B2 | 6/2011 | Ishihara et al. |
| 8,147,709 | B2 | 4/2012 | Mahler et al. |
| 8,198,491 | B2 | 6/2012 | Masatoshi et al. |
| 2010/0145112 | A1 | 6/2010 | Ishihara et al. |
| 2011/0097529 | A1 | 4/2011 | Durali et al. |
| 2011/0288346 | A1 * | 11/2011 | Poss et al. .................... 570/154 |

FOREIGN PATENT DOCUMENTS

| | | |
|---|---|---|
| JP | 2011-38054 A2 | 2/2011 |
| WO | WO 2010/095764 A1 | 8/2010 |

OTHER PUBLICATIONS

J.E. Bunch et al., "Aryl trifluoromethyl acetylenes," Journal of Fluorine Chemistry, 1987, vol. 36, No. 3, pp. 313-317.
W.G. Finnegan et al, "Improved Synthesis of 3,3,3-Trifluoropropyne," Journal of Organic Chemistry, 1963, vol. 28, pp. 1139-1140.
H.N. Miller et al., "Mono- and Di-Alkylacetylenes From Vicinal Dihalides and Sodium Amide in Liquid Ammonia," Journal of Organic Chemistry, 1954, vol. 19, No. 12, pp. 1882-1888.
A. Miyagawa et al., "Unusual Behavior of the Anionic Species from (E)-1-Chloro-3,3,3-trifluoropropene (HCFC-1233t)," European Journal of Organic Chemistry, 2009, vol. 2009, No. 26, pp. 4395-4399.
A.K. Brisdon et al., "Preparation and Functionalization of a Range of Main-Group Trifluoropropynyl Organometallic Compounds: The Application of Metalloid-Directed Carbolithiation to the Selective Synthesis of Novel Fluorocarbon Fragments," Organometallics, 2003, vol. 22, No. 26, pp. 5534-5542.
T. Hanamoto et al., "Generation and reactions of trifluoromethylethenyl titanium(II) species," Journal of Organic Chemistry, 2009, vol. 74, No. 19, pp. 7559-7561.
Alan R. Katritzky et al., "2-bromo-3,3,3-trifluoropropene: A facile trifluoromethylacetylene anion synthon," Journal of Fluorine Chemistry, 1996, vol. 80, No. 2, pp. 145-147.
R.N. Haszeldine, "The Reactions of Fluorocarbon Radicals. Part IV. The Synthesis of 3:3:3-Trifluoropropyne," Journal of the Chemical Society, 1951, pp. 588-591.
R.N. Haszeldine, "Reactions of Fluorocarbon Radicals. Part V. Alternative syntheses for trifluoromethylacetylene (3:3:3-trifluoropropyne), and the influence of polyfluoro-groups on adjacent hydrogen and halogen atoms," Journal of the Chemical Society, 1951, pp. 2495-2504.
R.N. Haszeldine, "Synthesis of 1:1:1 Trifluoropropyne," Nature, 1950, vol. 165, No. 4187, pp. 152-153.
A.L. Henne et al., "Trifluoropropyne," Journal of the American Chemical Society, 1951, vol. 73, No. 3, pp. 1042-1043.

\* cited by examiner

*Primary Examiner* — Jafar Parsa
(74) *Attorney, Agent, or Firm* — Erika S. Wilson

(57) ABSTRACT

In accordance with the present invention, processes of synthesizing 3,3,3-trifluoropropyne from 1,3,3,3-tetrafluoropropene, 1-chloro-3,3,3-trifluoropropene, and/or 1,1,1,3,3-pentafluoropropane are provided.

15 Claims, No Drawings

SYNTHESIS OF 3,3,3-TRIFLUOROPROPYNE

CROSS REFERENCE TO RELATED APPLICATION

The present application claims the benefit of U.S. Provisional Patent Application No. 61/745,078, filed on Dec. 21, 2012, the disclosure of which is incorporated herein by reference in its entirety.

FIELD OF THE INVENTION

The present invention relates to industrial-scale processes for the manufacture of 3,3,3-trifluoropropyne in commercial quantities.

BACKGROUND OF THE INVENTION

Chlorofluorocarbons (CFCs) are known and widely used in the industry as solvents, blowing agents, heat transfer fluid, aerosol propellants and other uses. But CFCs are also well-known to have ozone depletion potential (ODP) and are regulated by the Montreal Protocol. A suitable replacement material would have negligible or no ODP, as well as an acceptable global warming potential (GWP).

For example, 1-chloro-3,3,3-trifluoropropene (1233zd) is a chlorofluoroolefin with zero GWP and negligible ODP, which makes it very useful in foaming, aerosol and refrigeration applications. Cis-1233zd is much more preferred than its trans isomer (bp 18.7° C.) in solvent applications due to its higher boiling point of 39.4° C.

3,3,3-Trifluoropropyne (TFP) is another compound having zero GWP and negligible ODP, which also makes it potentially suitable for use in foaming agents, aerosol propellants, and refrigerants. However, there were no known industrial processes for making TFP in large quantities.

As set forth in US 2010/0145112, cis-1-chloro-3,3,3-trifluoropropene (cis-1233zd) may be treated with potassium hydroxide (KOH) to give TFP in good yield; however the trans isomer of 1233zd does not work well under these conditions (US 2010/0145112). 1,1,2-trichloro-3,3,3-trifluoropropene may be treated with zinc in DMF at 100° C. followed by hydrolysis with water to give 75% yield of 3,3,3-trifluoropropyne (J. Flu. Chem. 36(3), 313-17; 1987; J. Org. Chem. 1963, 28, 1139-40); however, the synthesis of 1,1,2-trichloro-3,3,3-trifluoropropene involves multistep reactions, and is not commercially available in large quantities.

It is noted that dehydrohalogenation of olefins is one of the most common reactions to make alkyne in small to medium quantities. For example, cis-1233zd may be easily dehydrochlorinated with 30% of KOH in methanol and water (1/1) to yield 90% of TFP at 38° C. (US2010/0145112). In contrast, the dehydrohalogenation of cis isomer (X=F, Cl) is not known to have been performed successfully with aqueous KOH or other base at variant temperature from 30° C. to 90° C. Trans-1233zd undergoes dehydrohalogenation at 50° C. with 20% KOH, but the yield is quite low since the proton in TFP is more acidic than the starting material.

Alkynes may also be obtained by dehydrobromination in good yield with sodium amide in liquid ammonia (J. Org. Chem. 1954, 1882). For example, cis-1233zd may be treated with lithium diisopropylamide (LDA) or methyl lithium at –80° C. to obtain trifluoroacetylenic lithium salt (Eur. J. Org. Chem. 2009, 4395-4399). This TFP lithium salt may also be obtained by deprotonating $CF_3CH_2CHF_2$ (245fa) with n-butyl lithium (Organomet. 2003, 5534) in ether.

Alternatively, 2-Bromo-3,3,3-trifluoropropene was often used as the precursor of TFP and could dehydrobrominated with LDA or n-butyllithium at 0° C., while hexamethylphosphoramide (HMPA) was used as a lithium salt stabilization agent (J. Org. Chem. 2009, 7559-61; J. Flu. Chem. 1996, 80, 145-7).

In another process, trifluoromethyliodide is coupled with acetylene at 200° C. to give 1-iodo-3,3,3-trifluoropropene in 70-80% yield, which could be then be dehydroiodinated to TFP at 70% yield (J. Chem. Soc. 1951, 588-91).

BRIEF SUMMARY OF THE INVENTION

In accordance with one aspect of the present invention, an improved production process for 3,3,3-trifluoropropyne (TFP) is provided in which a solution of 1-chloro-3,3,3-trifluoropropene in tetrahydrofuran is provided, and potassium tert-butoxide is added to the solution to yield TFP.

In accordance with another aspect of the present invention, an improved production process for 3,3,3-trifluoropropyne (TFP) is provided in which a compound selected from the group consisting of 1,3,3,3-tetrafluoropropene, 1-chloro-3,3,3-trifluoropropene, and 1,1,1,3,3-pentafluoropropane is mixed with a solvent, sodium amide is added to the mixture, and then hydrochloric acid is added to yield TFP.

In accordance with yet another aspect of the present invention, an improved production process for 3,3,3-trifluoropropyne (TFP) is provided in which a mixture comprising trans-1-chloro-3,3,3-trifluoropropene, the solution, and a catalyst is heated to yield TFP.

DETAILED DESCRIPTION

All the starting materials in this disclosure are commercially available. Sodium amide is commercially available, or may easily be made directly from ammonia and sodium metal with catalytic amount of iron chloride. Ammonia, diethyl ether or tetrahydrofuran are example solvents, and share the quality of being recyclable.

In accordance with the present invention, it was found that when 1,3,3,3-tetrafluoropropene (1234ze) or 1233zd was treated with strong base sodium amide at –25° C. in tetrahydrofuran (THF), sodium salt of 3,3,3-trifluoropropyne was obtained quantitatively, which can be hydrolyzed with water to give 3,3,3-trifluoropropyne in good yield. Both cis and trans isomers of 1234ze and 1233zd may be used under such conditions, as well as 1,1,1,3,3-pentafluoropropane (245fa).

The molar ratio of sodium amide to 1233zd or 1234ze should be at least 2, and can be higher, but ratios in excess of 3 were not particularly advantageous, and might result in greater incidence of side reactions. A particular preferred molar ratio is in the range of 2.1 to 2.2.

In an example embodiment, 1233zd is mixed with diethyl ether in a three-necked flask and cooled to –25° C. under nitrogen. $NaNH_2$ was added slowly through a solid addition funnel. After addition was complete, the mixture is stirred for another one to two hours at –25° C. before a diluted HCl solution is added. Product is collected in an –70° C. dry-ice acetone trap through a reflux condenser which is controlled at –5° C. to 0° C. The mixture is further refluxed for two hours after the hydrolysis to drive all TFP out.

The following examples further illustrate the present invention, but should not be construed to limit the scope of the invention in any way.

EXAMPLES

Example 1

106 g of 50% w/v KOH solution and 2.0 g of aliquat 336 in 600 mL stainless autoclave was diluted with 108 g of deionized water. The autoclave was sealed and vacuumed with nitrogen three times. 100 g of trans-1233zd was transferred into the autoclave and sealed. The mixture was heated to 50° C. for 20 hours. Sample in the gas phase was measured with gas chromatography (GC) to have 4.09% of 3,3,3-trifluoropropyne, 91.02% of trans-1233zd and other unidentified compounds.

Example 2

To 8.0 g of trans-1233zd in 100 mL of THF at −30° C. was added slowly sodium amide (5.8 g, 90%). The temperature was controlled below −20° C. by adding dry-ice into the acetone cooling bath. The mixture was stirred under nitrogen for another hour after addition. Then, diluted HCl solution was added at −20° C., and the product was collected in the −70° C. dry-ice acetone trap through a reflux condenser controlled at −5° C. to 0° C. The mixture was further refluxed for two hours after the hydrolysis to drive all TFP out. GC analysis showed 28.67% of 3,3,3-trifluoropropyne, 3.20% of trans-1233zd and 67.50% of THF.

Example 3

To 6.0 g of cis-1234ze in 60 mL of THF at −30° C. was added slowly sodium amide (5.5 g, 90%). The temperature was controlled below −20° C. by adding dry-ice into the acetone cooling bath. The mixture was stirred under nitrogen for another two hour after addition. Then, diluted HCl solution was added at −20° C., and the product was collected in the −70° C. dry-ice acetone trap through a reflux condenser controlled at −5° C. to 0° C. The mixture was further refluxed for two hours after the hydrolysis to drive all TFP out. 7.2 g clear liquid was collected. GC analysis showed 31.67% of 3,3,3-trifluoropropyne, 1.90% of trans-1233zd and 63.70% of THF.

Example 4

To 5.7 g of trans-1234ze in 80 mL of THF at −30° C. was added slowly sodium amide (4.5 g, 95%). The temperature was controlled below −20° C. by adding dry-ice into the acetone cooling bath. The mixture was stirred under nitrogen for another two hours after addition. Then, diluted HCl solution was added at −20° C., and the product was collected in the −70° C. dry-ice acetone trap through a reflux condenser controlled at −10° C. to −5° C. The mixture was further refluxed for two hours after the hydrolysis to drive all TFP out. 7.1 g clear liquid was collected. GC analysis showed 57.29% of 3,3,3-trifluoropropyne, 3.29% of trans-1233zd and 38.72% of THF.

Example 5

To 23.5 g of trans-1233zd in 80 mL of THF at 50-60° C. was added slowly potassium tert-butoxide (20.2 g) through a solid addition funnel. The temperature of the reflux condenser was controlled at −12° C. The product was collected in the −70° C. dry-ice acetone trap through the reflux condenser. After the tert-butoxide was added, the collected liquid in the cold trap was found by GC analysis to comprise 51.32% of 3,3,3-trifluoropropyne, 41.20% of trans-1233zd and 4.33% of THF.

What is claimed is:

1. A process of synthesizing 3,3,3-trifluoropropyne, the process comprising the steps of:
    providing a solution of 1-chloro-3,3,3-trifluoropropene in tetrahydrofuran; and,
    adding potassium tert-butoxide to the solution to yield the 3,3,3-trifluoropropyne.

2. The process of claim 1, wherein the solution of 1-chloro-3,3,3-trifluoropropene is at about 50-60° C. during the addition of potassium tert-butoxide to the solution.

3. The process of claim 1, wherein the 1-chloro-3,3,3-trifluoropropene is cis-1-chloro-3,3,3-trifluoropropene.

4. The process of claim 2, wherein the 1-chloro-3,3,3-trifluoropropene is cis-1-chloro-3,3,3-trifluoropropene.

5. A process of synthesizing 3,3,3-trifluoropropyne, the process comprising the steps of:
    providing a compound selected from the group consisting of 1,3,3,3-tetrafluoropropene, 1-chloro-3,3,3-trifluoropropene, and 1,1,1,3,3-pentafluoropropane;
    mixing the compound with a solvent to make a first mixture;
    adding sodium amide to the first mixture to make a second mixture;
    adding hydrochloric acid to the second mixture to yield the 3,3,3-trifluoropropyne.

6. The process of claim 5, wherein the compound is selected from the group consisting of 1,3,3,3-tetrafluoropropene and 1-chloro-3,3,3-trifluoropropene.

7. The process of claim 6, wherein the majority of the compound is in a cis form.

8. The process of claim 6, wherein the majority of the compound is in a trans form.

9. The process of claim 6, wherein the molar ratio of sodium amide to the compound in the first mixture is 2 or greater.

10. The process of claim 9, wherein the molar ratio of sodium amide to the compound in the first mixture is between 2 and 3.

11. A process of synthesizing 3,3,3-trifluoropropyne, the process comprising the steps of:
    providing a solution comprising potassium hydroxide; and,
    heating a first mixture comprising trans-1-chloro-3,3,3-trifluoropropene, the solution, and a catalyst to yield the 3,3,3-trifluoropropyne.

12. The process of claim 11, wherein the first mixture is heated to at least 50° C. for at least 20 hours.

13. The process of claim 11, wherein the solution comprising potassium hydroxide comprises at least 20% potassium hydroxide.

14. The process of claim 11, wherein the solution comprising potassium hydroxide comprises the catalyst.

15. The process of claim 14, wherein the catalyst is aliquat 336.

* * * * *